(12) United States Patent
Breazzano et al.

(10) Patent No.: US 9,107,728 B2
(45) Date of Patent: Aug. 18, 2015

(54) EYEBALL STABILIZING APPARATUS AND METHOD OF USE

(71) Applicants: Mark Philip Breazzano, Manlius, NY (US); Sidney T. Malak, Atlanta, GA (US)

(72) Inventors: Mark Philip Breazzano, Manlius, NY (US); Sidney T. Malak, Atlanta, GA (US)

( * ) Notice: Subject to any disclaimer, the term of this patent is extended or adjusted under 35 U.S.C. 154(b) by 166 days.

(21) Appl. No.: 14/034,297

(22) Filed: Sep. 23, 2013

(65) Prior Publication Data

US 2014/0114410 A1    Apr. 24, 2014

Related U.S. Application Data

(60) Provisional application No. 61/704,524, filed on Sep. 23, 2012.

(51) Int. Cl.
*A61F 9/00* (2006.01)
*A61F 9/007* (2006.01)
*A61F 2/14* (2006.01)
*A61F 2/00* (2006.01)

(52) U.S. Cl.
CPC . *A61F 9/007* (2013.01); *A61F 2/14* (2013.01); *A61F 2/141* (2013.01); *A61F 2/0095* (2013.01); *A61F 2/148* (2013.01)

(58) Field of Classification Search
CPC ....... A61F 2/148; A61F 2/143; A61F 2/1662; A61F 9/007; A61B 19/20; A61B 19/201
USPC ......... 606/107; 248/121, 122.1, 125.2, 177.1, 248/178.1; 623/4.1, 6.64; 269/289 R; 428/16
See application file for complete search history.

(56) References Cited

U.S. PATENT DOCUMENTS

| | | | | |
|---|---|---|---|---|
| 2,572,416 A * | 10/1951 | Wilson | | 623/6.64 |
| 3,480,971 A * | 12/1969 | Smith | | 623/6.64 |
| 3,651,689 A * | 3/1972 | Haddad | | 600/398 |
| 4,706,666 A * | 11/1987 | Sheets | | 606/107 |
| 4,737,132 A * | 4/1988 | Shunsaku | | 446/348 |
| 4,994,080 A * | 2/1991 | Shepard | | 623/6.64 |
| 5,026,392 A * | 6/1991 | Gordon | | 623/6.64 |
| 5,137,459 A * | 8/1992 | Zirm | | 434/271 |
| 5,171,254 A * | 12/1992 | Sher | | 606/166 |
| 5,267,553 A * | 12/1993 | Graether | | 600/236 |
| 5,584,880 A * | 12/1996 | Martinez | | 623/6.64 |
| 5,725,493 A * | 3/1998 | Avery et al. | | 604/9 |
| 6,007,881 A * | 12/1999 | Lennard | | 428/16 |
| 6,197,056 B1 * | 3/2001 | Schachar | | 623/4.1 |
| 6,419,698 B1 * | 7/2002 | Finger | | 623/6.64 |
| 6,514,223 B1 * | 2/2003 | Feinsod | | 604/1 |
| 8,083,794 B2 * | 12/2011 | Liu | | 623/6.64 |
| 8,118,867 B2 * | 2/2012 | Perry et al. | | 623/6.64 |
| 2001/0047205 A1 * | 11/2001 | Garonzik | | 623/6.64 |
| 2002/0035345 A1 * | 3/2002 | Beck | | 604/20 |
| 2002/0055753 A1 * | 5/2002 | Silvestrini | | 606/166 |
| 2002/0138089 A1 * | 9/2002 | Gutierrez Ortega et al. | | 606/166 |
| 2003/0078607 A1 * | 4/2003 | Carriazo | | 606/166 |
| 2003/0109885 A1 * | 6/2003 | Tano | | 606/107 |
| 2003/0114861 A1 * | 6/2003 | Carriazo | | 606/107 |
| 2003/0120200 A1 * | 6/2003 | Bergheim et al. | | 604/27 |
| 2004/0073303 A1 * | 4/2004 | Schanzlin et al. | | 623/5.16 |
| 2004/0196430 A1 * | 10/2004 | Graham | | 351/178 |

(Continued)

*Primary Examiner* — Eduardo C Robert
*Assistant Examiner* — Stuart S Bray
(74) *Attorney, Agent, or Firm* — Schmeiser, Olsen & Watts, LLP (57) ABSTRACT

An adjustable apparatus for stabilizing an eyeball suitable for use during surgical or transplant procedures is disclosed. Furthermore, an associated method is also provided.

20 Claims, 10 Drawing Sheets

(56) References Cited

U.S. PATENT DOCUMENTS

| | | | |
|---|---|---|---|
| 2004/0215126 A1* | 10/2004 | Ahmed | 604/9 |
| 2004/0254420 A1* | 12/2004 | Ward | 600/37 |
| 2005/0196741 A1* | 9/2005 | Otto | 434/271 |
| 2006/0069434 A1* | 3/2006 | Durette | 623/6.64 |
| 2006/0235428 A1* | 10/2006 | Silvestrini | 606/107 |
| 2006/0247659 A1* | 11/2006 | Moeller et al. | 606/107 |
| 2007/0027538 A1* | 2/2007 | Aharoni et al. | 623/6.12 |
| 2007/0244367 A1* | 10/2007 | Caffey et al. | 600/178 |
| 2007/0282282 A1* | 12/2007 | Wong et al. | 604/294 |
| 2007/0282405 A1* | 12/2007 | Wong et al. | 607/104 |
| 2008/0046078 A1* | 2/2008 | Singer | 623/6.64 |
| 2008/0091224 A1* | 4/2008 | Griffis et al. | 606/166 |
| 2008/0221677 A1* | 9/2008 | Alfaro | 623/6.64 |
| 2008/0275461 A1* | 11/2008 | Nallakrishnan | 606/107 |
| 2010/0152646 A1* | 6/2010 | Girijavallabhan et al. | 604/22 |
| 2011/0066239 A1* | 3/2011 | Smoot et al. | 623/6.64 |
| 2011/0109107 A1* | 5/2011 | Lin | 294/1.2 |
| 2011/0152774 A1* | 6/2011 | Lopez et al. | 604/165.04 |
| 2011/0257638 A1* | 10/2011 | Boukhny et al. | 606/4 |
| 2012/0051042 A1* | 3/2012 | Artsyukhovich et al. | 362/231 |
| 2013/0060254 A1* | 3/2013 | Juhasz et al. | 606/107 |
| 2013/0103145 A1* | 4/2013 | John et al. | 623/6.12 |
| 2013/0123916 A1* | 5/2013 | Nigam et al. | 623/5.11 |
| 2013/0317609 A1* | 11/2013 | Green et al. | 623/6.64 |
| 2014/0052140 A1* | 2/2014 | Sayegh | 606/107 |
| 2015/0102187 A1* | 4/2015 | Hennessey et al. | 248/122.1 |

* cited by examiner

EYEBALL STABILIZING APPARATUS AND METHOD OF USE

CROSS REFERENCE TO RELATED APPLICATION

This application claims priority to U.S. Provisional Application No. 61/704,524 filed Sep. 23, 2012, which is incorporated herein in its entirety.

FIELD OF TECHNOLOGY

The following relates to an apparatus for stabilizing an eyeball and more specifically to embodiments of an adjustable, globe-conforming ocular stabilizer suitable for use during surgical or transplant procedures.

BACKGROUND

Precision and stability are of paramount importance during any surgical or transplant procedures. Because of the delicacy and intricate nature of the human eye, these factors become especially important during any ocular procedures, including removal of the cornea. However, for the same reasons, stability can be difficult to achieve when dealing with even donated eyeballs.

Thus, a need exists for an apparatus and method for adequately stabilizing a human eyeball during corneal cutting and similar procedures, which is also suitably designed so as to avoid or reduce damage to the rest of the eyeball.

SUMMARY

A first aspect relates generally to an eyeball stabilizing apparatus comprising resting bowl having a concaved surface, wherein the concaved surface is configured to conform to a human eyeball; a structural base, operatively attached to the resting bowl and including at least one securing-force support member, the at least one securing-force support member configured to support and facilitate operation of at least one securing-force applicator; and an adjustable container configured to receive the eyeball and stabilize the eyeball in a non-abrasive fashion, the adjustable container being operatively attached to the resting bowl so as to be able to open and receive the eyeball, and so as to contract and conform to and securely stabilize the eyeball, when the securing force is applied to the adjustable container by the at least one securing force applicator.

A second aspect relates generally to an ocular globe-conforming eyeball stabilizing apparatus comprising: a concaved resting bowl, the resting bowl including an opening, the opening configured to receive an optic nerve of an eyeball; a structural base, operatively attached to the resting bowl and configured so as to provide room for the optic nerve when it is received within the opening of the resting bowl; and an adjustable container operably attached to the resting bowl and configured to receive the eyeball and optic nerve, wherein the adjustable container includes a plurality of globally conforming contact points configured to globally conform to the eyeball when a securing-force is applied to the adjustable container to contract the adjustable container in a uniform manner to stabilize an eyeball in a non-abrasive fashion.

A third aspect relates generally to a method for stabilizing an eyeball comprising: providing an eyeball; providing an eyeball stabilizing device, the eyeball stabilizing device including: a resting bowl having a concaved surface, wherein the concaved surface is configured to conform to a human eyeball; a structural base, operatively attached to the resting bowl and including at least one securing-force support member, the at least one securing-force support member configured to support and facilitate operation of at least one securing-force applicator; and an adjustable container configured to receive the eyeball and stabilize the eyeball in a non-abrasive fashion, the adjustable container being operatively attached to the resting bowl so as to be able to open and receive the eyeball, and so as to contract and conform to and securely stabilize the eyeball, when the securing force is applied to the adjustable container by the at least one securing force applicator; and applying a securing force to the adjustable container, the securing force applied by at least one securing-force applicator; wherein the application of the securing force upon the adjustable container causes the adjustable container to globally contract and conform to the eyeball to stabilize an eyeball in a non-abrasive fashion The foregoing and other features of construction and operation will be more readily understood and fully appreciated from the following detailed disclosure, taken in conjunction with accompanying drawings.

BRIEF DESCRIPTION OF THE DRAWINGS

Some of the embodiments will be described in detail, with reference to the following figures, wherein like designations denote like members, wherein.

DETAILED DESCRIPTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure.

As a preface to the detailed description, it should be noted that, as used in this specification and the appended claims, the singular forms "a", "an" and "the" include plural referents, unless the context clearly dictates otherwise.

Figure 1:
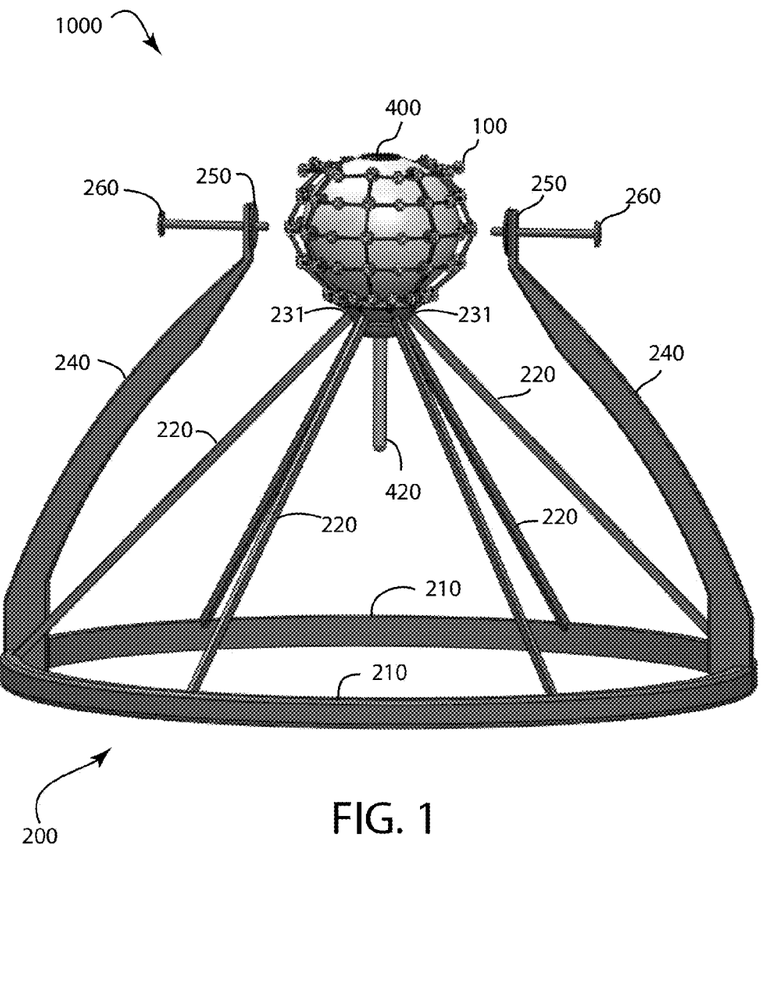
FIG. 1 depicts a side view of a first embodiment of an ocular globe-conforming stabilization device.

Referring to the drawings, FIG. 1 depicts an embodiment 1000 of an ocular globe-conforming stabilization device. An embodiment of a stabilization device 1000 may include an adjustable container 100 such as a cage, support system, or matrix, a structural foundation or base 200.

The adjustable container 100 may be configured to surround a human eye 400 and may be capable of being adjusted to fit the size of the eye. As shown more clearly in FIGS. 6, 9 and 10, embodiments of an adjustable container 100 may be structurally based on or similar to a Hoberman sphere design, where the cage may expand or contract while maintaining its shape. This expandability allows the adjustable container 100 to fit securely to and stabilize eyes of different sizes, and also allows for a user to insert an eyeball 400 into the ocular globe-conforming device without any fear of scraping, abrasion, friction, or other damaging contact with the adjustable container 100. The spherical contraction also uniformly distributes the pressure around the eyeball 400 during contraction, preventing damage to the eyeball 400 and thus increasing the potential that the eyeball 400 can be saved for future use and research following the initial procedure.

Figure 2:
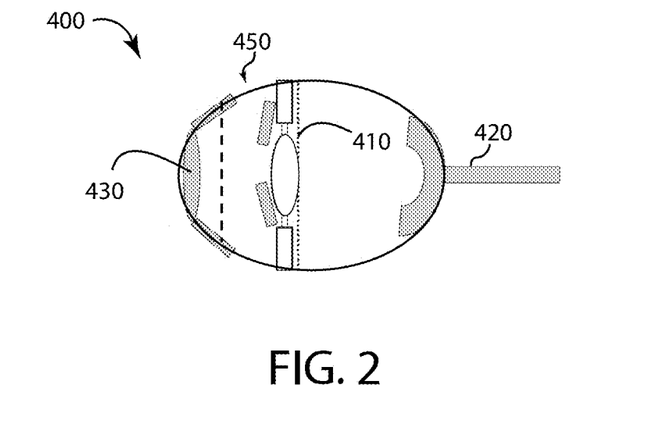
FIG. 2 depicts a side view of a schematic of a human eye.
Figure 6:
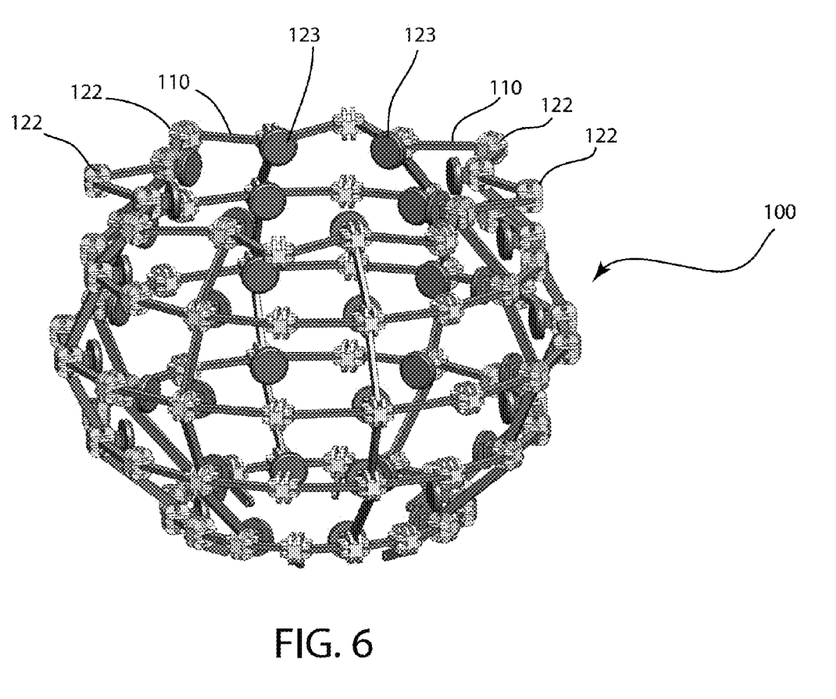
FIG. 6 depicts a side view of an embodiment of an adjustable container.
Figure 9:
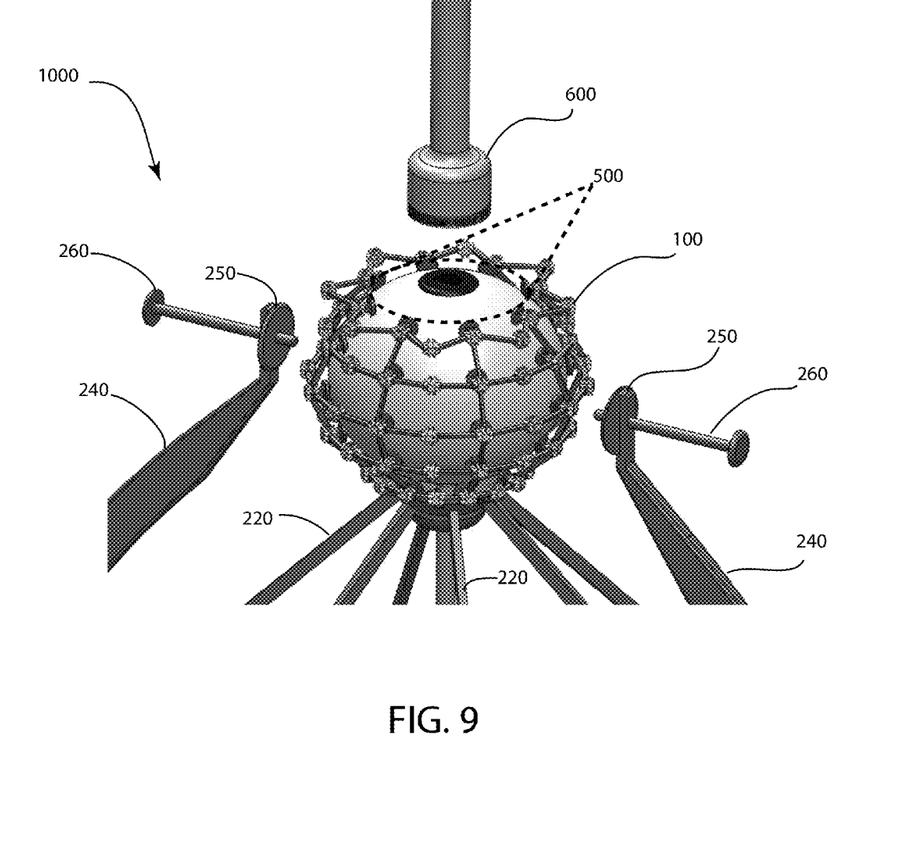
FIG. 9 depicts an overhead perspective view of an embodiment of an ocular globe-conforming stabilization device with a human eyeball being stabilized.
Figure 10:
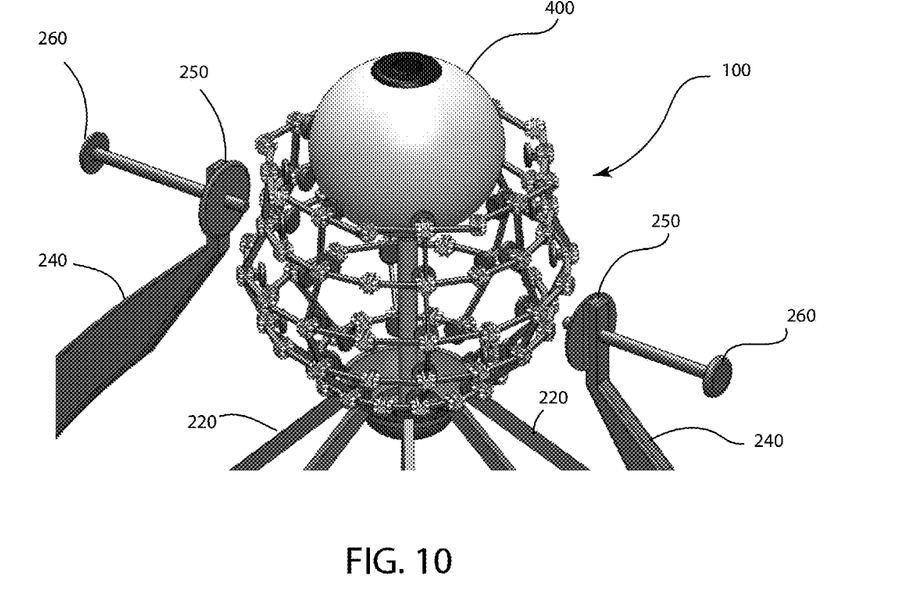
FIG. 10 depicts a top perspective view of an embodiment of an ocular globe-conforming stabilization device.

With reference still to FIGS. 6, 9 and 10, the adjustable container 100 may be slightly elliptical to accommodate the only roughly-spherical dimensions of the human eye 400. As depicted in FIG. 2, the dimensions of a typical eye 400 are greater horizontally than vertically, while the visual (anterior-posterior) axis 410 can be highly variable. As discussed above, the ability of the adjustable container 100 to expand reduces the risk of damage occurring during insertion into or removal from the adjustable container 100, and the ability to conform to the eyeball 400 also distributes the stabilizing force to prevent damage.

The adjustable container 100 may be made of any material that may adequately withstand and conduct the securing-force generated during the contracting of the adjustable container 100 and the ocular globe-conforming stabilization device. By way of example only, various plastics, polymers, metals, alloys, composites, or natural materials such as woods may be used to create components individually or in used in combination. Materials may also be chosen for their durability, resistance to wear, rust, corrosion, etc., light weight, amenity to sanitization, or aesthetic appeal.

Figure 3:
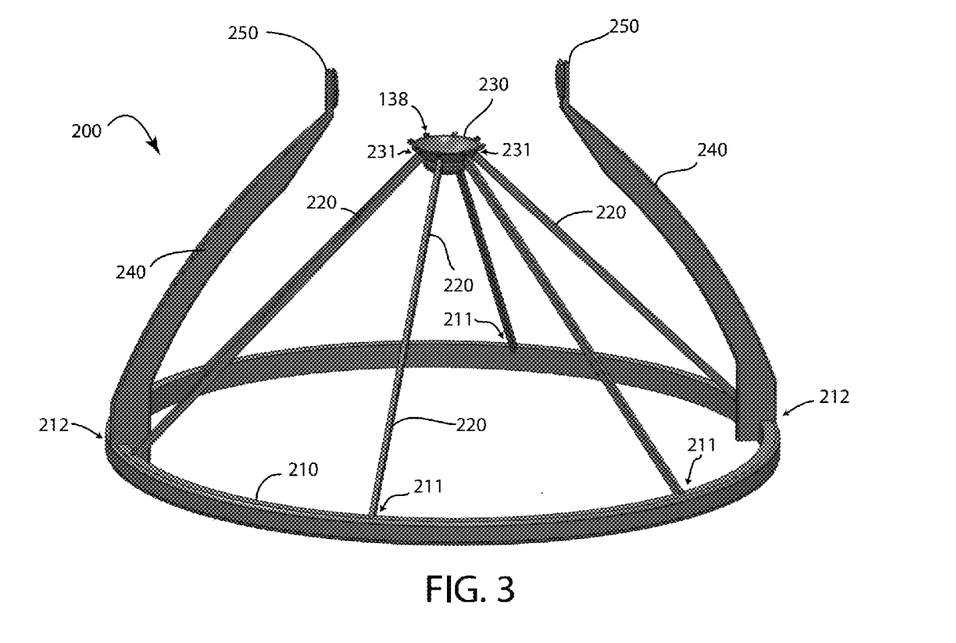
FIG. 3 depicts a side view of a first embodiment of a structural or base of an embodiment of an ocular globe-conforming stabilization device.

Referring now to FIG. 3, an embodiment of the structural foundation 200 may include any of the following: a structural foundation base 210, at least one resting surface support 220, a resting surface or bowl 230, and one or more securing-force supports 240.

Similarly to the adjustable container, the structural foundation or base 200, the resting surface or bowl 230, the securing-force supports 240, and the resting surface supports 220 may be made of any material capable of adequately supporting the weight and/or securing-force generated by the embodiment 1000. By way of example only, various plastics, polymers, metals, alloys, composites, or natural materials such as woods may be used. Again, materials may also be chosen for their durability, resistance to wear, rust, corrosion, etc., light weight, amenity to sanitization, or aesthetic appeal.

The resting surface supports 220 may connect to the structural foundation base 210 by a connection point 211. Similarly, the securing-force supports 240 may connect to the structural base 210 by at least connection point 212. Embodiments of these connection points 211 and 212 include various fastening and connecting devices or methods among which may be a direct joinder of the materials comprising the structural base 210 and the resting surface support 220, or the structural base 210 and the securing-force support 240.

Additionally, the resting bowl 230 may be connected to the resting bowl supports 220 by at least one connection point 231. Embodiments of these connection points 231 again include various fastening and connecting devices and methods among which may be a direct joinder of the materials comprising the resting surface support 220 and the resting surface or bowl 230, such as by welding, joinder through a friction-type snap-fit, or joinder using fastening devices such as screws, bolts, rivets, etc., as will be known by those of ordinary skill in the art.

Figure 4A:
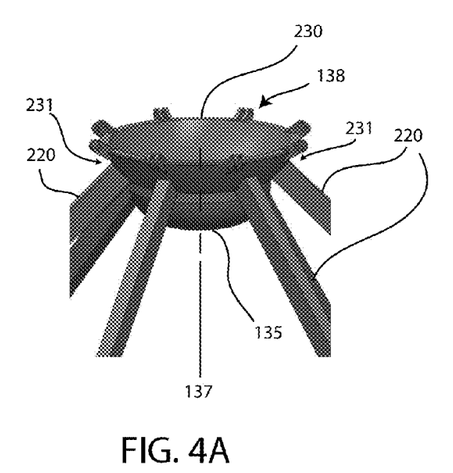
FIG. 4A depicts side view of an embodiment of connection points between a structural foundation or base and an adjustable container.
Figure 4B:
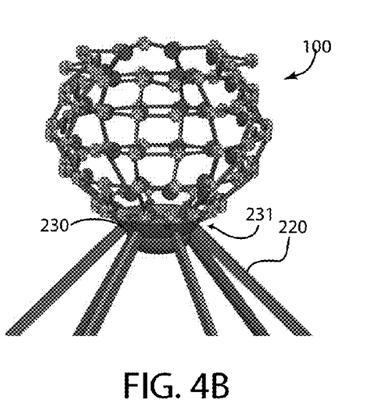
FIG. 4B depicts a side view of an embodiment of connection points between a structural foundation or base and an adjustable container.
Figure 4C:
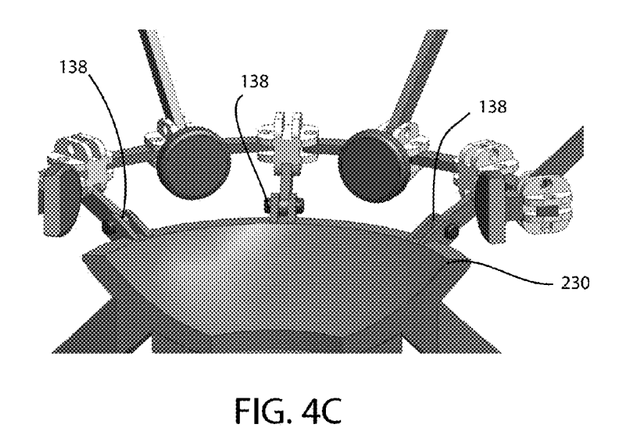
FIG. 4C depicts an enlarged side view of an embodiment of connection points between a structural foundation or base and an adjustable container.
Figure 5A:
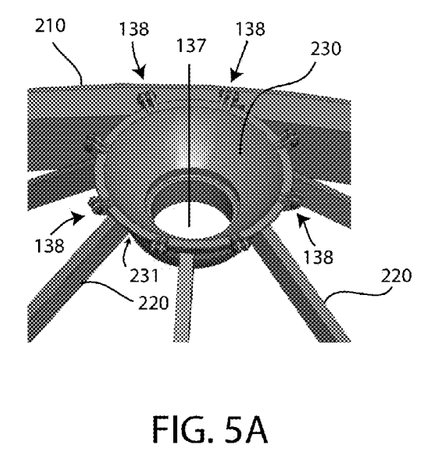
FIG. 5A depicts an overhead perspective view of an embodiment of a structural foundation or base.
Figure 5B:
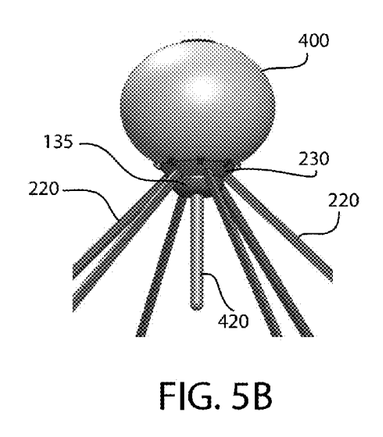
FIG. 5B depicts a side view of an embodiment of a structural foundation or base.

With reference now to FIG. 4A, the resting bowl or surface 230 has a generally concave shape, designed to conform to an average human eye 400. The resting bowl or surface 230 may be attached to the structural base 210 by at least one resting surface support 220. The resting surface support 220 may connect to the resting bowl 230 at a location commensurate with at least one connection point 231, and to the structural base 210 at a location commensurate with at least one connection point 211.

With reference now to both FIGS. 2 and 4A, the resting surface or bowl 230 may also contain an optic nerve clearance opening 137 to allow room for the optic nerve 420 of an eyeball 400. This optic nerve clearance opening 137 allows the optical nerve 420 to remain attached to the eyeball 400, eliminating the potential for damage to the eyeball 400 that may occur during removal of the optic nerve 420, by eliminating the need to remove the optic nerve 420 during some procedures. Instead, through the use of an optic nerve clearance opening 137, the optic nerve 420 may be left intact without hindering stability or the operation. In a further embodiment, the optic nerve clearance opening 137 may be surrounded by a contractible ring 135 which can expand or contract to fit tightly around the optic nerve 420. This contractible ring 135 may be contracted to tightly grip the optic nerve 420, providing yet another point of stability in an ocular globe-conforming stability device. Thus a contractible ring 137 further reduces the potential for damage to an eyeball during any procedure. A contractible ring 135 may take the form of various embodiments capable of receiving the optic nerve 420 and contracting to secure the nerve 420. In one embodiment this contractible ring 135 may comprise a simple resilient ring, such as a stretchable bushing or O-ring, having a clearance opening 137 that may be opened wide enough to receive the optic nerve 420 and then tightened and closed down upon the optic nerve 420 to secure it in place.

With reference now to FIGS. 4A, 4B, 4C and 5A, in an embodiment 1000, the resting surface or bowl 230 may also be a point at which the structural foundation 200 is connected to the adjustable container 100. The resting bowl or surface 230 may be attached to the adjustable container 100 by the use of fasteners, connectors or joints 138. The fasteners, connectors, or joints may be comprised of any suitable material in any suitable design facilitating operable movement of the components attached to the resting bowl 230. In an embodiment, the fasteners, connectors, or joints 138 are operatively attached so as to pivot the adjustable container 100 in relation to the resting bowl or surface 230. This ability to pivot allows the adjustable container 100 to further conform to the shape of a typical eyeball 400, while also increasing the ability to distribute the securing-force or pressure around the entirety of the eyeball 400, thereby simultaneously increasing the stability provided and reducing the potential for damage as is more thoroughly discussed above.

Figure 7:
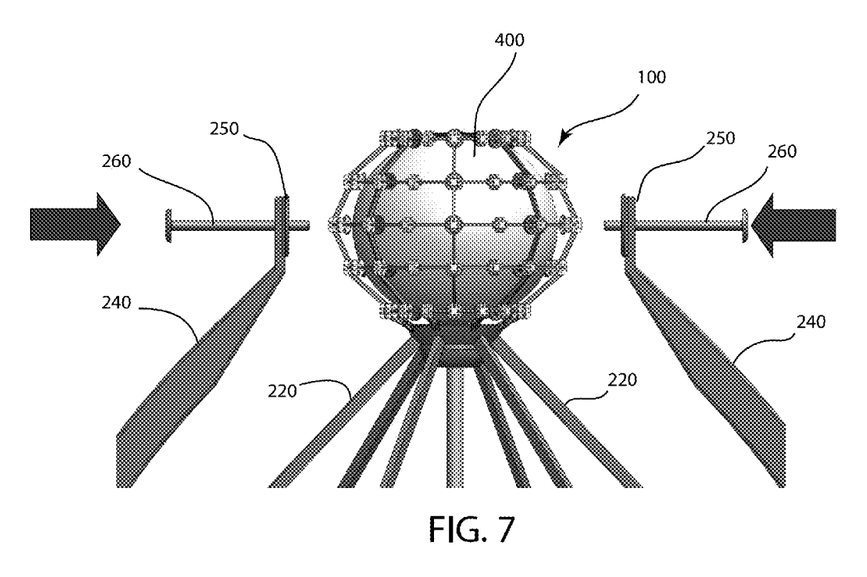
FIG. 7 depicts a side view of an embodiment of an ocular globe-conforming stabilization device.

As shown in FIGS. 3 and 7, the securing-force supports 240 may extend to be adjacent to the resting bowl 230 and/or the adjustable container 100. While the resting surface or bowl 230 may be supported in various positions on the structural foundation 200; however, in one embodiment the support is located at the apex of the structural foundation 200.

Referring now to FIG. 7, the securing-force support 240 may also include one or more guide holes, grooves, or tracks 250. These guide holes, grooves, or tracks 250 may be used to operationally direct a securing-force applicator 260. The securing-force applicators 260 may include such embodiments as screws, knobs, keys, levers, switches, or gears; however, those skilled in the art understand that various other devices may be used to effectuate various methods of applying securing-force upon the adjustable container 100. By way of example only, the securing-force applicators 260 may be designed to be turned, screwed, rotated, pushed, pulled, levered, cranked, or ratcheted in order to apply securing-force to the adjustable container 100.

When the securing-force applicators 260 are utilized to apply force to the adjustable container 100, such force may result in a uniform, spherical contraction of the adjustable container 100. For example, embodiments fashioned similar to a Hoberman sphere would be well understood by those having skill in the art, to contract uniformly as securing force is applied. This uniform, spherical contraction of the adjustable container 100 may cause the interior of the adjustable container 100 to contact the eyeball 400. However, as discussed above, because of the nature of the spherical contraction, such contact may be distributed evenly across a broad amount of the surface of the eyeball 400, reducing the stress of the contracting force, and preventing damage to the eyeball 400.

An ocular globe-conforming stabilization device 1000 may utilize one or more points of force to contract the adjustable container 100 in the rigid, uniform manner described above. For, example, as depicted in FIG. 7, in one embodiment, the securing-force may be applied by the securing-force applicator 260 in the form of a simple screw or bolt.

While various placements of the securing-force supports 240, guide holes, grooves, or tracks 250, and securing-force applicators 260 are contemplated, in one embodiment two securing-force supports 240, corresponding guide holes, grooves, or tracks 250, and securing-force applicators 260 may be used and placed at diametric points (180 degrees) on the structural foundation 200 or adjustable container 100. Such a configuration may provide the maximal stabilization. Those of ordinary skill in the art understand that other embodiments may be utilized, such as placing any securing-force supports 240, corresponding guide holes, grooves, or tracks 250, and securing-force applicators 260 at various other angles around the adjustable container (for example, using four sets placed at 90° intervals, or three sets located at 120° intervals), or placing the securing-force supports 240, corresponding guide holes, grooves, or tracks 250, and securing-force applicators 260 in non-planar or non-symmetrical arrangements around the adjustable container, so that the securing force applied effectuates contraction or closing of the adjustable container 100 in a manner that minimizes damage to an eyeball 400. As demonstrated by the varying embodiments recited, the ocular globe-conforming stabilization device may include any number, configuration, or orientation of securing-force supports 240, guide holes, grooves, or tracks 250, and securing-force applicators 260.

Figure 8:
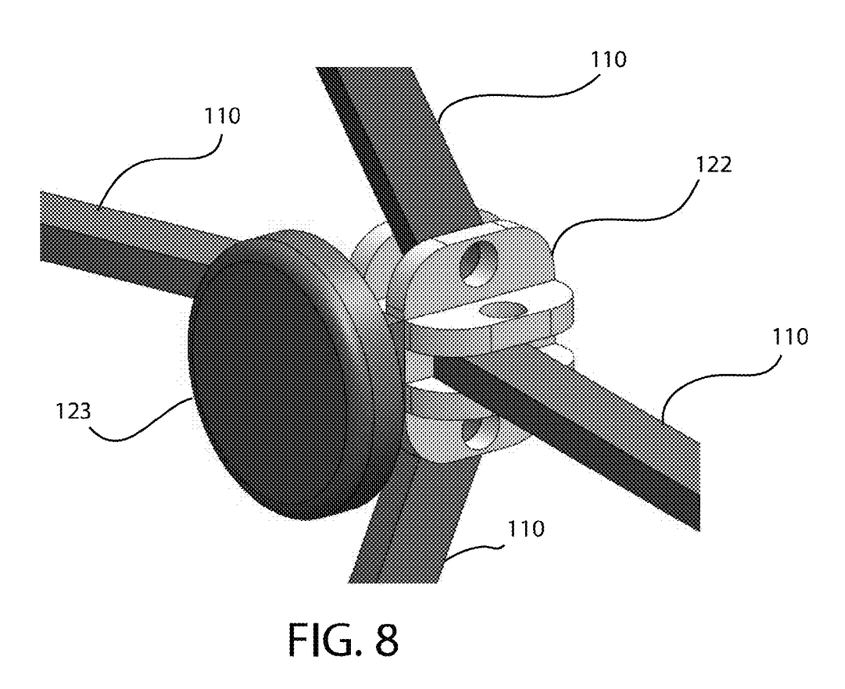
FIG. 8 depicts a side view of an embodiment of a section of an adjustable container.

Referring now to FIGS. 6 and 8, the adjustable container 100 may be comprised of multiple cross-pieces 110. Embodiments of the cross-pieces 110 may include various components such as posts, sections, bars, pieces, or arms, which may be connected to each other in interlocking patterns by any type of fastener, connector, or joint 122. An embodiment of the fasteners, connectors, or joints 122 may be a pivot joint. The cross-pieces 110 and the fasteners, connectors, or joints 122 may be made of any suitable material suitably durable to withstand and conduct the securing-force generated by the stabilization process. By way of example only, various plastics, polymers, metals, alloys, composites, or natural materials such as woods may be used. Materials may also be chosen for their durability, resistance to wear, rust, corrosion, etc., light weight, amenity to sanitization, or aesthetic appeal.

With reference still to FIGS. 6 and 8, the fasteners, connectors, or joints 122 of the adjustable container 100 may have the capability of pivoting, flexing, rotating, or swiveling through any plane in three-dimensional space. This pivoting, flexing, rotating, or swiveling may allow the adjustable container 100 to conform to any eyeball 400 while still providing stabilizing pressure or force. Further, the pivoting, flexing, rotating, or swiveling may also reduce any strain, friction, or abrasion that might result on the eyeball 400 during insertion into, removal from, or during stabilizing by, the adjustable container 100 and the ocular globe-conforming stabilization device 1000.

With continued reference to FIGS. 6 and 8, the adjustable container 100 may contact the eyeball at various contact points 123. These contact points 123 may located on the interior surface of the fasteners, connectors, or joints 122 to provide the most flexibility during contraction and to achieve the most conforming arrangements during use of the ocular globe-conforming device. In addition to being located on the interior surface of the fasteners, connectors, or joints 122 (which may have the capacity of pivoting, flexing, rotating, or swiveling as described above), in a further embodiment of the contact points 123, they may be comprised of pads, buffers, or cushions to even further reduce the impact of the adjustment container's contact with the human eye 400 during contraction and stabilization.

As depicted in FIG. 6, the contact points (or pads, buffers, or cushions) 123 may be positioned uniformly around the interior of the adjustable container 100 in order to more evenly distribute the compressive force on the eyeball 400. The adjustable container 100 and the contact points 123 may be globally conforming and configured so as to provide minimal abrasion to the eyeball 400. In such embodiments, the adjustable container 100 may contract uniformly in a spherical manner so as to avoid any scraping, rubbing, chafing, sliding, or dragging contact between the eyeball 400 and the contact points 123. Due to the spherical contraction of the adjustable container 100, as well as flexibility of the contact points 123, the securing-force is distributed gently and evenly around a large portion of the body of the eyeball 400, thus minimizing the stress, friction, and impact on any one portion of the eyeball 400 and also reducing the overall impact on the structure of the eyeball 400 itself.

Referring back to FIG. 9, in an embodiment 1000, the ocular globe-conforming stabilization device includes a cutting access region 500. The cutting-access-region 500 may be an open region above the adjustable container 100 that allows full access and visibility to the anterior segment 450 of the eyeball 400, and specifically to the cornea 430, to allow access for a surgical or transplant procedure. During operation, a cutting device 600 may be employed to access the eyeball 400 through the cutting-access-region 500. In an embodiment of the ocular globe-conforming stabilization device 1000, the cutting-access-region 450 may be large enough to permit access to only the corneal area 430 of the eyeball 400, or may permit access to the entire anterior segment 450 of the eyeball 400, or to an even larger area of the eyeball 400. Further, the cutting-access-region 500 may be large enough to permit access of multiple cutting devices 600 during use.

As depicted in FIG. 9, the adjustable container 100 may be fully contracted onto the eyeball 400, providing maximal stability for a procedure. Due to the adjustable nature of the adjustable container 100 and the flexibility of the contact points 123, such contraction and stabilization may be accomplished with minimized friction, abrasion, scraping, sliding, and dragging between the eyeball 400 and the adjustable container 100. Further, the contact points 123 may comprise pads, buffers, or cushions to soften the impact with, and cushion the securing-force generated by, the contraction of the adjustable container 100.

As shown in FIG. 10, the adjustable container 100 may be manipulated into a fully expanded configuration, allowing an eyeball 400 to be inserted into or removed from the ocular globe-conforming stabilization device 1000 with minimized friction, abrasion, scraping, or various other stresses upon the eyeball 400.

While this disclosure has been described in conjunction with the specific embodiments outlined above, it is evident that many alternatives, modifications and variations will be apparent to those skilled in the art. Accordingly, the preferred embodiments of the present disclosure as set forth above are intended to be illustrative, not limiting. Various changes may be made without departing from the spirit and scope of the invention, as required by the following claims. The claims provide the scope of the coverage of the invention and should not be limited to the specific examples provided herein.

What is claimed is:

1. An eyeball stabilizing apparatus comprising:
   a resting bowl having a concaved surface, wherein the concaved surface is configured to conform to a human eyeball;
   a structural base, operatively attached to the resting bowl and including at least one securing-force support member, the at least one securing-force support member configured to support and facilitate operation of at least one securing-force applicator; and
   an adjustable container configured to receive the eyeball and stabilize the eyeball in a non-abrasive fashion, the adjustable container being operatively attached to the resting bowl so as to be able to open and receive the eyeball, and so as to contract and conform to and securely stabilize the eyeball, when the securing force is applied to the adjustable container by the at least one securing force applicator.

2. The apparatus of claim 1, wherein the adjustable container is comprised of interconnected, independently pivoting contact points.

3. The apparatus of claim 1, wherein the adjustable container, when it is conformed to the shape of an eyeball, has a shape similar to a Hoberman sphere.

4. The apparatus of claim 1, wherein the adjustable container is configured so as to maintain a spherical shape during contraction.

5. The apparatus of claim 1, wherein the adjustable container is configured to maintain an elliptical shape during contraction.

6. The apparatus of claim 1, wherein the adjustable container further comprises a plurality of globally conforming contact points configured so as to provide minimal abrasion to the eyeball when the adjustable devices secures the eyeball.

7. An ocular globe-conforming eyeball stabilizing apparatus comprising:
   a concaved resting bowl, the resting bowl including an opening, the opening configured to receive an optic nerve of an eyeball;
   a structural base, operatively attached to the resting bowl and configured so as to provide room for the optic nerve when it is received within the opening of the resting bowl; and
   an adjustable container operably attached to the resting bowl and configured to receive the eyeball and optic nerve, wherein the adjustable container includes a plurality of globally conforming contact points configured to globally conform to the eyeball when a securing-force is applied to the adjustable container to contract the adjustable container in a uniform manner to stabilize an eyeball in a non-abrasive fashion.

8. The apparatus of claim 7, wherein the adjustable container is comprised of interconnected, independently pivoting contact points.

9. The apparatus of claim 7, wherein the adjustable container, when it is conformed to the shape of an eyeball, has a shape similar to a Hoberman sphere.

10. The apparatus of claim 7, wherein the adjustable container is configured so as to maintain a spherical shape during contraction.

11. The apparatus of claim 7, wherein the adjustable container is configure so as to maintain an elliptical shape during contraction.

12. The apparatus of claim 7, wherein the adjustable container includes a cutting access region, when the adjustable container is contracted, to allow full access and visibility to an anterior segment of the eyeball.

13. The apparatus of claim 7, further comprising two securing force applicators positioned around the adjustable container at 180° intervals and configured to exert force upon the adjustable container.

14. A method of stabilizing an eyeball comprising;
   providing an eyeball,
   providing an eyeball stabilizing device, the eyeball stabilizing device including:
      a resting bowl having a concaved surface, wherein the concaved surface is configured to conform to a human eyeball;
      a structural base, operatively attached to the resting bowl and including at least one securing-force support member, the at least one securing-force support member configured to support and facilitate operation of at least one securing-force applicator; and
      an adjustable container configured to receive the eyeball and stabilize the eyeball in a non-abrasive fashion, the adjustable container being operatively attached to the resting bowl so as to be able to open and receive the eyeball, and so as to contract and conform to and securely stabilize the eyeball, when the securing force is applied to the adjustable container by the at least one securing force applicator; and
   applying a securing force to the adjustable container, the securing force applied by at least one securing-force applicator;
   wherein the application of the securing force upon the adjustable container causes the adjustable container to globally contract and conform to the eyeball to stabilize an eyeball in a non-abrasive fashion.

15. The method of claim 14, wherein the adjustable container is comprised of interconnected, independently pivoting contact points.

16. The method of claim 14, wherein the adjustable container, when it is conformed to the shape of an eyeball, has a shape similar to a Hoberman sphere.

17. The method of claim 14, wherein the adjustable container is configured so as to maintain a spherical shape during contraction.

18. The method of claim 14, wherein the adjustable container is configure so as to maintain an elliptical shape during contraction.

19. The method of claim 14, wherein the adjustable container includes a cutting access region, when the adjustable container is contracted, to allow full access and visibility to an anterior segment of the eyeball.

20. The method of claim 14, wherein the adjustable container further comprises a plurality of globally conforming contact points configured so as to provide minimal abrasion to the eyeball when the adjustable devices secures the eyeball.

\* \* \* \* \*